United States Patent [19]

Maurer et al.

[11] Patent Number: 4,535,091
[45] Date of Patent: Aug. 13, 1985

[54] O-PYRAZOLYL-N-CYANOALKYLSULPHE-NYL-CARBAMATE PESTICIDES

[75] Inventors: Fritz Maurer, Wuppertal; Bernhard Homeyer, Leverkusen; Benedikt Becker, Mettmann, all of Fed. Rep. of Germany

[73] Assignee: Bayer Aktiengesellschaft, Leverkusen, Fed. Rep. of Germany

[21] Appl. No.: 589,290

[22] Filed: Mar. 14, 1984

[30] Foreign Application Priority Data

Mar. 24, 1983 [DE] Fed. Rep. of Germany ....... 3310831

[51] Int. Cl.³ .................. A01N 43/56; C07D 231/18
[52] U.S. Cl. ...................................... 514/407; 548/375
[58] Field of Search .............................. 548/375, 377; 424/273 P

[56] References Cited

U.S. PATENT DOCUMENTS 4,418,073 11/1983 Maurer et al. .................. 424/273 P Primary Examiner—Richard A. Schwartz
Assistant Examiner—Kurt G. Briscoe Attorney, Agent, or Firm—Sprung, Horn, Kramer & Woods

[57] ABSTRACT

The invention relates to new O-(pyrazol-4-yl) N-(α-cyanoalkylsulphenyl)-carbamates of the general formula (I)

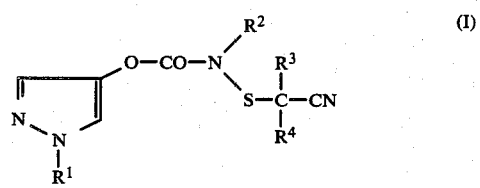

in which
R¹ represents alkyl or cycloalkyl,
R² represents alkyl and
R³ and R⁴ each represent alkyl or together represent an alkylene radical linked in two places,
which can be used as agents for combating pests.

6 Claims, No Drawings

O-PYRAZOLYL-N-CYANOALKYLSULPHENYL-CARBAMATE PESTICIDES

The invention relates to new O-(pyrazol-4-yl)-N-(α-cyanoalkylsulphenyl)-carbamates, several processes for their preparation and their use in agents for combating pests, in particular in insecticides, acaricides and nematicides.

It is known that certain O-pyrazolyl-N-sulphenyl-carbamates, such as, for example, O-(1-isopropyl-pyrazol-4-yl)-N-methyl-N-(4-methylphenylsulphenyl)-carbamate, O-(1-isopropylpyrazol-4-yl)-N-dichlorofluoromethylsulphenyl-N-methyl-carbamate, O-(1-t-butylpyrazol-4-yl) N-methyl-N-trichloromethylsulphenyl-carbamate, O-(1-t-butylpyrazol-4-yl)-N-methyl-N-phenylsulphenyl-carbamate or O-(t-butylpyrazol-4-yl)-N-(t-butylsulphenyl)-N-methyl-carbamate, have insecticidal properties (compare European Patent No. 43,917).

However, the insecticidal action of these compounds is not always satisfactory, especially in the case of low concentrations of active compound and when low amounts of active compound are applied.

New O-(pyrazol-4-yl)-N-(α-cyanoalkylsulphenyl)-carbamates of the general formula (I)

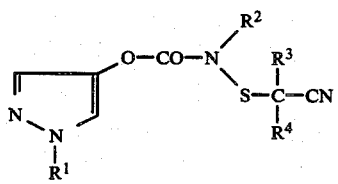

in which
R$^1$ represents alkyl or cycloalkyl,
R$^2$ represents alkyl and
R$^3$ and R$^4$ each represent alkyl or together represent an alkylene radical linked in two places,
have been found.

It has furthermore been found that the new O-(pyrazol-4-yl)-N-(α-cyanoalkylsulphenyl)-carbamates of the general formula (I)

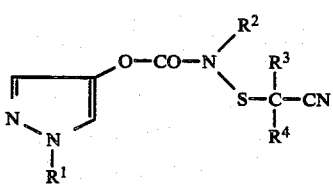

in which
R$^1$ represents alkyl or cycloalkyl,
R$^2$ represents alkyl and
R$^3$ and R$^4$ each represent alkyl or together represent an alkylene radical linked in two places,
are obtained by a process in which
(a) 4-hydroxypyrazoles of the formula (II)

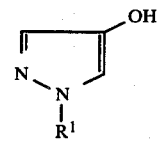

in which R$^1$ has the abovementioned meaning, are reacted with N-sulphenylated carbamoyl halides of the formula

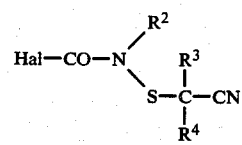

in which
R$^2$, R$^3$ and R$^4$ have the abovementioned meaning and
Hal represents halogen,
if appropriate using a diluent and if appropriate in the presence of an acid acceptor, or in which
(b) O-pyrazol-4-yl carbamates of the formula (IV)

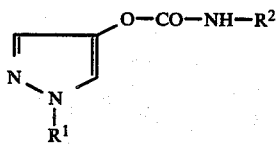

in which R$^1$ and R$^2$ have the abovementioned meaning, are reacted with sulphenyl halides of the formula (V)

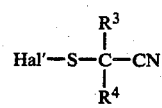

in which
R$^3$ and R$^4$ have the abovementioned meaning and
Hal' represents halogen,
if appropriate using a diluent and if appropriate in the presence of an acid acceptor.

The new O-(pyrazol-4-yl) N-(α-cyanoalkylsulphenyl)-carbamates of the formula (I) are distinguished by a high activity as agents for combating pests, in particular by a high insecticidal and nematicidal activity.

Surprisingly, the O-(pyrazol-4-yl) N-(α-cyanoalkylsulphenyl)-carbamates of the formula (I) according to the invention have a considerably more powerful insecticidal and nematicidal activity than known compounds of similar structure and the same type of action, such as, for example, the abovementioned compounds, that is to say O-(1-isopropylpyrazol-4-yl) N-methyl-N-(4-methylphenylsulphenyl)-carbamate, O-(1-isopropylpyrazol-4-yl)-N-dichlorofluoromethyl-sulphenyl-N-methyl-carbamate, O-(1-t-butylpyrazol-4-yl)-N-methyl-N-trichloromethyl-sulphenyl-carbamate, O-(t-butylpyrazol-4-yl)-N-methyl-N-phenylsulphenyl-carbamate and O-(1-t-butylpyrazol-4-yl)-N-(t-butylsulphenyl)-N-methyl-carbamate.

Alkyl R$^1$, R$^2$ and R$^3$ denotes straight-chain or branched alkyl with preferably 1 to 8, in particular 1 to 6 and particularly preferably 1 to 4, carbon atoms, examples including methyl, ethyl, n- and i-propyl, n-, i-, s- and t-butyl and 1,1-dimethylpropyl.

Cycloalkyl $R^1$ preferably denotes cycloalkyl with 3 to 7, in particular 3, 5 or 6, carbon atoms, examples which may be mentioned being cyclopropyl, cyclobutyl, cyclopentyl, cyclohexyl and cycloheptyl.

The alkylene radical formed by $R^3$ and $R^4$ can be straight-chain or branched and preferably contains 4 to 7 carbon atoms, examples which may be mentioned being ethylene, propylene and butylene.

Hal and Hal' represent fluorine, chlorine, bromine or iodine, preferably fluorine, chlorine or bromine, in particular fluorine or chlorine.

Formula (I) provides a general definition of the O-(pyrazol-4-yl) N-(α-cyanoalkylsulphenyl)-carbamates according to the invention.

Preferred compounds of the formula (I) are those in which
$R^1$ represents straight-chain or branched alkyl with up to 8 carbon atoms or cycloalkyl with 3 to 8 carbon atoms,
$R^2$ represents straight-chain or branched alkyl with up to 6 carbon atoms and
$R^3$ and $R^4$ each represent straight-chain or branched alkyl with up to 6 carbon atoms or together represent an alkylene radical which has 4 to 7 carbon atoms and is linked in two places.

Particularly preferred compounds of the formula (I) are those in which
$R^1$ represents straight-chain or branched alkyl with 1 to 6 carbon atoms or cyclopropyl, cyclopentyl, cyclohexyl or cycloheptyl,
$R^2$ represents straight-chain or branched alkyl with 1 to 4 carbon atoms and
$R^3$ and $R^4$ each represent straight-chain or branched alkyl with 1 to 4 carbon atoms or together represent a $-(CH_2)_n-$ radical,
wherein n represents the number 4 or 5.

If, for example, 4-hydroxy-1-isopropyl-pyrazole and N-(2-cyanoprop-2-yl-sulphenyl) N-methyl-carbamoyl fluoride are used as starting substances, the course of the reaction in process (a) according to the invention can be represented by the following equation:

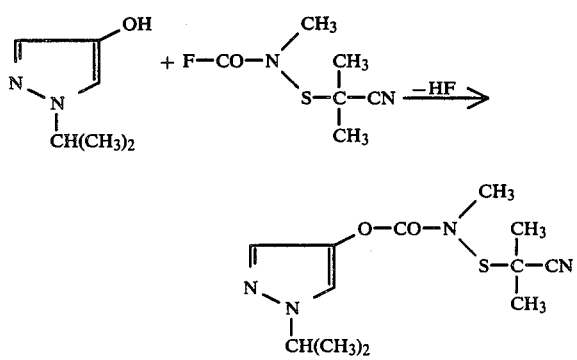

If, for example, O-(1-t-butylpyrazol-4-yl) N-methyl-carbamate and 2-cyanoprop-2-yl-sulphenyl chloride are used as starting substances, the course of the reaction in process (b) according to the invention can be represented by the following equation:

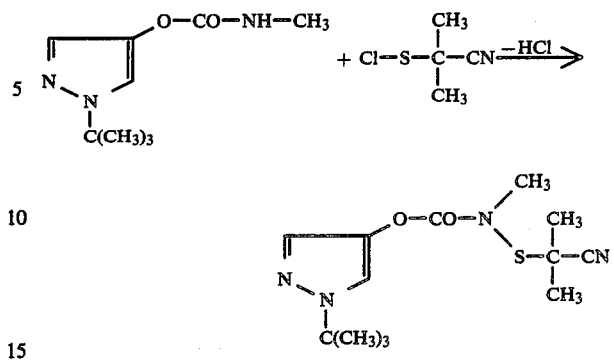

Formula (II) provides a general definition of the 4-hydroxypyrazoles to be used as starting substances for the process according to the invention. In this formula (II), $R^1$ has the same meaning as has been given above in the description of the substances of the formula (I) according to the invention.

Examples which may be mentioned of compounds of the formula (II) are: 1-methyl-, 1-ethyl-, 1-n-propyl-, 1-iso-propyl-, 1-(1,1-dimethyl-propyl)-, 1-(2,2-dimethylpropyl)-, 1-n-butyl-, 1-sec.-butyl-, 1-tert.-butyl-, 1-(1-methylbutyl)-, 1-(2-methylbutyl)-, 1-(3-methylbutyl)-, 1-n-pentyl-, 2-(1-ethylpropyl)-, 1-cyclopropyl-, 1-cyclobutyl-, 1-cyclopentyl- and 1-cyclohexyl-4-hydroxypyrazole.

The 4-hydroxypyrazoles of the formula (II) are known (compare Liebigs Ann. Chem. 313, (1900), 17 and DE-OS (German Published Specification) No. 2,931,033).

The 4-hydroxy-pyrazoles of the formula (II) are obtained, for example, by reacting the corresponding 4-methoxypyrazoles with hydrobromic acid. The 4-methoxypyrazoles can be prepared in a known manner, for example by reacting corresponding hydrazines with 2-methoxy-3-dimethyl-amino-acrolein (compare Archiv der Pharmazie 300, (1967), 704–708).

Formula (III) provides a general definition of the N-sulphenylated carbamoyl halides also to be used as starting substances for process (a) according to the invention. In this formula (III), $R^2$, $R^3$ and $R^4$ have the same meaning as has been given in the description of the substances of the formula (I) according to the invention. Hal preferably represents fluorine or chlorine.

Examples which may be mentioned of the compounds of the formula (III) are:

$$\text{Hal}-\text{CO} - \text{N} \begin{matrix} R^2 \\ R^3 \\ \text{S}-\text{C}-\text{CN} \\ R^4 \end{matrix} \quad (III)$$

Hal = fluorine or chlorine.

| $R^2$ | $R^3$ | $R^4$ |
|---|---|---|
| CH₃ | CH₃ | CH₃ |
| C₂H₅ | CH₃ | CH₃ |
| i-C₃H₇ | CH₃ | CH₃ |
| t-C₄H₉ | CH₃ | CH₃ |
| CH₃ | CH₃ | C₂H₅ |
| C₂H₅ | CH₃ | C₂H₅ |
| i-C₃H₇ | CH₃ | C₂H₅ |
| t-C₄H₉ | CH₃ | C₂H₅ |
| CH₃ | CH₃ | i-C₃H₇ |
| C₂H₅ | CH₃ | i-C₃H₇ |

-continued $$\text{Hal}-\text{CO}-\text{N}\begin{array}{c}R^2\\\diagdown\\S-C-CN\\|\\R^4\end{array}R^3 \quad (III)$$

Hal = fluorine or chlorine.

| R² | R³ | R⁴ |
|---|---|---|
| i-C₃H₇ | CH₃ | i-C₃H₇ |
| t-C₄H₉ | CH₃ | i-C₃H₇ |
| CH₃ | —CH₂—CH₂—CH₂—CH₂— | |
| C₂H₅ | —CH₂—CH₂—CH₂—CH₂— | |
| i-C₃H₇ | —CH₂—CH₂—CH₂—CH₂— | |
| t-C₄H₉ | —CH₂—CH₂—CH₂—CH₂— | |
| CH₃ | —CH₂—CH₂—CH₂—CH₂—CH₂— | |
| C₂H₅ | —CH₂—CH₂—CH₂—CH₂—CH₂— | |

The N-sulphenylated carbamoyl halides of the formula (III) are known (compare DE-OS (German Published Specification) No. 3,109,028 and European Patent No. 25,014).

The sulphenylated carbamoyl halides of the formula (III) are obtained, for example, by reacting the corresponding sulphenyl halides with N-substituted carbamoyl halides in the presence of a diluent, such as, for example, toluene, and in the presence of an acid acceptor, such as, for example, triethylamine, at temperatures between −10° and 100° C.

Formula (IV) provides a general definition of the O-pyrazol-4-yl carbamates to be used as starting substances for process (b) according to the invention. In this formula (IV), $R^1$ and $R^2$ have the same meaning as has been given in the description of the substances of the formula (I) according to the invention.

Examples which may be mentioned of the compounds of the formula (IV) are: O-(1-isopropyl-pyrazol-4-yl) N-n-propyl-, O-(1-tert.-butyl-pyrazol-4-yl) N-ethyl-, O-(1-isopropyl-pyrazol-4-yl) N-iso-propyl-, O-(1-isopropyl-pyrazol-4-yl) N-ethyl-, O-(1-sec.-butyl-pyrazol-4-yl) N-n-propyl-, O-(1-(2-methyl-2-butyl)-pyrazol-4-yl) N-ethyl-, O-(1-(2-methyl-2-butyl)-pyrazol-4-yl) N-n-propyl-, O-(1-n-propyl-pyrazol-4-yl) N-ethyl-, O-(1-(2-methyl-2-butyl) N-isopropyl-, O-(1-ethyl-pyrazol-4-yl) N-ethyl-, O-(1-cyclohexyl-pyrazol-4-yl) N-ethyl-, O-(1-sec.-butyl-pyrazol-4-yl) N-ethyl-, O-(1-methyl-pyrazol-4-yl) N-ethyl-, O-(1-cyclopropyl-pyrazol-4-yl) N-ethyl- and (1-tert.-butyl-pyrazol-4-yl) N-n-propyl-carbamate.

The compounds of the formula (IV) are known (compare DE-OS (German Published Specification) No. 3,114,833; EP-OS (European Published Specification) No. 43,917).

The compounds of the formula (IV) are obtained, for example, by reacting 4-hydroxy-pyrazoles of the formula (II) with corresponding isocyanates in the presence of a diluent, such as, for example, acetone, methylene chloride or toluene, and if appropriate in the presence of a catalyst, such as, for example, triethylamine, at temperatures between 10° and 80° C., or with phosgene and the corresponding amines in the presence of a diluent, such as, for example, toluene, and if appropriate in the presence of an acid acceptor, such as, for example, triethylamine, at temperatures between −10° and 80° C.

Formula (V) provides a general definition of the sulphenyl halides also to be used as starting substances for process (b) according to the invention. In this formula (V), $R^3$ and $R^4$ have the same meaning as has been given in the description of the substances of the formula (I) according to the invention. Hal' preferably represents fluorine or chlorine.

Examples which may be mentioned of compounds of the formula (V) are: 2-cyanoprop-2-yl-, 2-cyanobut-2-yl-, 2-cyanopent-2-yl-, 2-cyanohex-2-yl-, 3-cyanopent-3-yl-, 3-cyanohex-3-yl-, 3-cyanohept-3-yl-, 4-cyanohept-3-yl-, 2-cyano-3-methylbut-2-yl-, 2-cyano-3,3-dimethylbut-2-yl-, 3-cyano-2,4-dimethylpent-3-yl-, 1-cyano-cyclopentyl- and 1-cyanocyclohexyl-sulphenyl fluoride and -sulphenyl chloride.

The sulphenyl halides of the formula (V) are known (compare U.S. Pat. No. 3,832,378).

Preparation processes (a) and (b) according to the invention are preferably carried out using diluents. Possible diluents are virtually all the inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethylsulphoxide, tetramethylene sulphone and hexamethylphosphoric acid triamide. Toluene is preferably used as the diluent.

All the customary acid-binding agents can be used as acid acceptors. Alkali metal carbonates and alcoholates, such as sodium and potassium carbonate and sodium and potassium methylate and ethylate, and furthermore aliphatic, aromatic or heterocyclic amines, for example triethylamine, trimethylamine, dimethylaniline, dimethylbenzylamine, pyridine and diazabicycloundecene, have proved particularly suitable. Triethylamine is preferably used as the acid acceptor. The reaction temperature can be varied within a substantial range. In general, the reaction is carried out between −20° and 100° C.; preferably at 0° to 80° C.

Processes (a) and (b) according to the invention are in general carried out under normal pressure.

The starting substances are usually employed in equivalent amounts for carrying out processes (a) and (b) according to the invention. An excess of one or the other of the reactants provides no substantial advantages. The reaction is in general carried out in a suitable diluent in the presence of an acid acceptor, and the reaction mixture is stirred at the required temperature for several hours. If necessary, a water-immiscible organic solvent, for example toluene, is then added and the organic phase is worked up in the customary manner, by washing, drying and distilling off the solvent. The products are thus obtained in the form of oils or crystals. They are characterized by their melting point or refractive index.

Some of the new compounds are obtained in the form of oils, some of which cannot be distilled without decomposition, but can be freed from the last volatile constituents by so-called "incipient distillation", that is to say by prolonged heating to moderately elevated temperatures under reduced pressure, and can be purified in this manner. They are characterized by their refractive index.

Besides a good insecticidal and nematicidal action, the O-(pyrazol-4-yl) N-(α-cyanoalkylsulphenyl)-carbamates of the formula (I) according to the invention also show a good action against hygiene pests and pests of stored products.

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and *Scutigera* spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum,* Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia Litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterabra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Demanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic materials, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms, and others.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

PREPARATION EXAMPLES

EXAMPLE 1

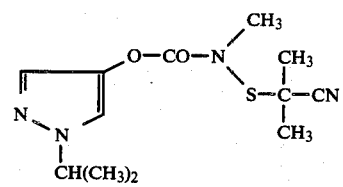

12 g (0.075 mole) of N-(2-cyanoprop-2-ylsulphenyl)-N-methyl-carbamoyl fluoride are added dropwise to a mixture of 9.45 g (0.075 mole) of 4-hydroxy-1-isopropylpyrazole, 8.5 g (0.085 mole) of triethylamine and 100 ml of toluene at 25° C. When the addition has ended, the mixture is stirred at room temperature for 18 hours. For working up, the reaction mixture is washed twice with water, dried over sodium sulphate and freed from the solvent in vacuo. 18 g (85% of theory) of O-(1-isopropylpyrazol-4-yl) N-(2-cyanoprop-2-ylsulphenyl)-N-methyl-carbamate are obtained in the form of a yellow oil of refractive index $n_D^{21}$ 1.5070.

The following compounds of the formula (I) are obtained in a corresponding manner and in accordance with the general preparation conditions:

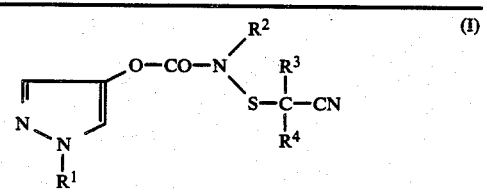

| Example No. | $R^1$ | $R^2$ | $R^3$ | $R^4$ | Refractive index |
|---|---|---|---|---|---|
| 2 | t-C$_4$H$_9$ | CH$_3$ | CH$_3$ | CH$_3$ | $n_D^{21}$ 1.5050 |
| 3 | CH$_3$ | CH$_3$ | CH$_3$ | CH$_3$ | |
| 4 | C$_2$H$_5$ | CH$_3$ | CH$_3$ | CH$_3$ | |
| 5 | t-C$_4$H$_9$ | C$_2$H$_5$ | CH$_3$ | CH$_3$ | |
| 6 | C$_2$H$_5$-C(CH$_3$)(CH$_3$)- | CH$_3$ | CH$_3$ | CH$_3$ | |
| 7 | c-C$_6$H$_{11}$ | CH$_3$ | CH$_3$ | CH$_3$ | |
| 8 | t-C$_4$H$_9$ | CH$_3$ | —CH$_2$—CH$_2$—CH$_2$—CH$_2$— | | |
| 9 | t-C$_4$H$_9$ | i-C$_3$H$_7$ | CH$_3$ | CH$_3$ | |
| 10 | s-C$_4$H$_9$ | CH$_3$ | CH$_3$ | CH$_3$ | |

USE EXAMPLES

The compounds below are used as comparison substances in the use examples which follow:

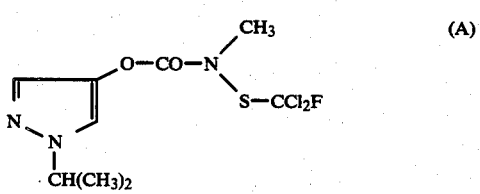

O-(1-Isopropylpyrazol-4-yl) N-dichlorofluoromethyl-sulphenyl-N-methyl-carbamate

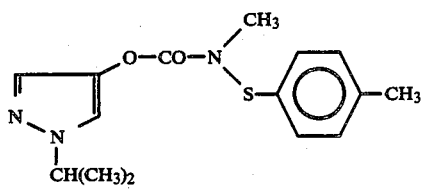

(B)

O-(1-Isopropylpyrazol-4-yl)N-methyl-N-(4-methyl-phenylsulphenyl)-carbamate

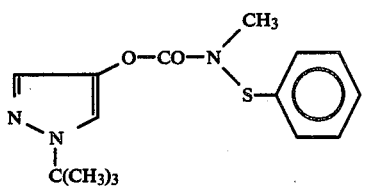

(C)

O-(1-t-Butylpyrazol-4-yl)N-methyl-N-phenylsulphenylcarbamate

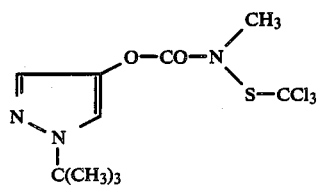

(D)

O-(1-t-Butylpyrazol-4-yl)N-methyl-N-trichloromethyl-sulphenyl-carbamate

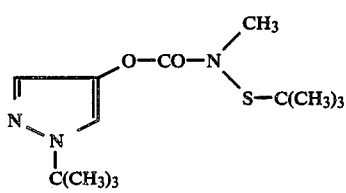

(E)

O-(1-t-Butylpyrazol-4-yl)N-(t-butylsulphenyl)-N-methyl-carbamate.

EXAMPLE A

Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/liter being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compound according to preparation example (2) shows a superior action compared to the prior art.

EXAMPLE B

Root-systemic action
Test insect: *Phaedon cochleariae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/liter) being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the mortality figures. It is 100% if all the test insects have been killed and 0% if just as many test insects are still alive as in the case of the untreated control.

In this test, for example, the following compounds from the preparation examples show a superior action compared to the prior art: 1 and 2.

EXAMPLE C

Root-systemic action
Test insect: *Myzus persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/liter) being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the mortality figures. It is 100% if all the test insects have been killed and 0% if just as many test insects are still alive as in the case of the untreated control.

In this test, for example, the following compounds from the preparation examples show a superior action compared to the prior art: 1 and 2.

EXAMPLE D

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount of active compound per unit volume of soil, which is given in ppm, being decisive. The treated soil is filled into pots, lettuce is sown in and the pots are kept at a greenhouse temperature of 27° C.

After four weeks, the lettuce roots are examined for infestation with nematodes (root galls), and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, the compound according to preparation example (2) shows a superior action compared to the prior art.

EXAMPLE E

Drosophila test
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

1 cm³ of the preparation of the active compound is pipetted onto a filter paper disc (7 cm diameter). The wet disc is placed over the opening of a glass vessel containing 50 vinegar flies (*Drosophila melanogaster*) and is covered with a glass plate.

After the specified periods of time, the destruction in % is determined. 100% means that all the flies have been killed; 0% means that none of the flies have been killed.

In this test, for example, the compounds according to preparation example 2 shows a superior activity compared to the prior art.

EXAMPLE F

Doralis test (systemic action)
Solvent: 3 parts by weight
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Vicia faba*) which have been heavily infested with the bean aphid (*Doralis fabae*) are each watered with 20 ml of the preparation of the active compound of the desired concentration in such a way that the preparation of the active compound penetrates into the soil without wetting the shoot. The active compound is taken up by the roots and passes to the shoot.

After specified periods of time, the destruction in % is determined. 100% means that all the aphids have been killed; 0% means that none of the aphids have been killed.

In this test, for example, the following compounds from the preparation examples show a superior activity compared to the prior art: 1 and 2.

EXAMPLE G

Tetranychus test (resistant)
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified periods of time, the destruction in % is determined. 100% means that all the spider mites have been killed; 0% means that none of the spider mites have been killed.

In this test, for example, the compounds from the preparation example 2 shows a superior activity compared to the prior art.

It will be appreciated that the instant specification and examples are set forth by way of illustration and not limitation, and that various modifications and changes may be made without departing from the spirit and scope of the present invention.

What is claimed is:

1. An O-(pyrazol-4-yl) N-(α-cyanoalkylsulphenyl)-carbamate of the formula

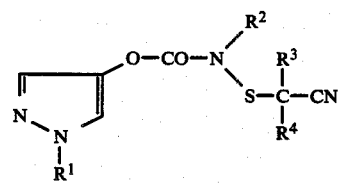

in which
R¹ is $C_1$–$C_8$-alkyl or $C_3$–$C_8$-cycloalkyl,
R² is $C_1$–$C_6$-alkyl and
R³ and R⁴ each independently is $C_1$–$C_6$-alkyl or together are a $C_4$–$C_7$-alkylene radical.

2. A compound according to claim 1 wherein such compound is O-(1-isopropyl-pyrazol-4-yl) N-2-cyano-prop-2-ylsulphenyl)-N-methyl-carbamate of the formula 3. A compound according to claim 1 wherein such compound is O-(1-t-butyl-pyrazol-4-yl) N-(2-cyanoprop-2-ylsulphenyl)-N-methyl-carbamate of the formula

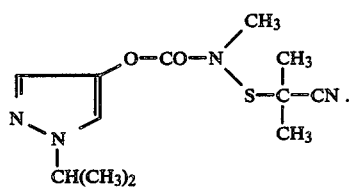

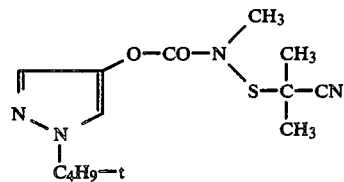

4. An insecticidal, acaricidal or nematicidal composition comprising an insecticidally, acaricidally or nematicidally effective amount of a compound according to claim 1 in admixture with a diluent.

5. A method of combating insects, acarids or nematodes which comprises administering to such insects, acarids or nematodes or a habitat thereof an insecticidally, acaricidally or nematicidally effective amount of a compound according to claim 1.

6. The method according to claim 5, wherein such compound is
O-(1-isopropyl-pyrazol-4-yl) N-(2-cyanoprop-2-ylsulphenyl)-N-methyl-carbamate, or
O-(1-t-butyl-pyrazol-4-yl) N-(2-cyanoprop-2-ylsulphenyl)-N-methyl-carbamate.

* * * * *